US 6,730,085 B2

(12) United States Patent
George et al.

(10) Patent No.: US 6,730,085 B2
(45) Date of Patent: May 4, 2004

(54) SURGICAL BIOPSY INSTRUMENT

(76) Inventors: Samuel George, 4 Ronneby Close, Weybridge, Surrey (GB), KT13 9SB; Yusuf Abrahams, "Lake View", Sandy Lane, Northwood, Middlesex (GB), HA6 3ES ( * ) Notice: Subject to any disclaimer, the term of this patent is extended or adjusted under 35 U.S.C. 154(b) by 179 days.

(21) Appl. No.: 09/935,877

(22) Filed: Aug. 23, 2001

(65) Prior Publication Data

US 2002/0049441 A1 Apr. 25, 2002

Related U.S. Application Data

(63) Continuation of application No. PCT/GB00/00645, filed on Feb. 23, 2000.

(30) Foreign Application Priority Data

Feb. 24, 1999 (GB) .............................................. 9904258

(51) Int. Cl.[7] .............................................. A61B 18/18
(52) U.S. Cl. .............................. 606/47; 606/41; 606/45; 606/49; 600/564
(58) Field of Search .............................. 606/30, 31, 32, 606/33, 34, 35, 36, 37, 38, 39, 40, 41, 42, 43, 44, 45, 46, 47, 48, 49, 50, 51, 52; 600/564

(56) References Cited

U.S. PATENT DOCUMENTS 5,324,288 A 6/1994 Billings et al.
5,554,159 A 9/1996 Fischer
5,676,663 A 10/1997 Kim

FOREIGN PATENT DOCUMENTS

| DE | 1516414 A | 6/1969 |
| DE | 2613778 A | 10/1977 |
| NL | 1004723 C | 6/1998 |
| WO | WO-87/05486 A | 9/1987 |
| WO | WO-95/20922 A | 8/1995 |

*Primary Examiner*—Rosiland Rollins
(74) *Attorney, Agent, or Firm*—Lerner, David, Littenberg, Krumholz & Mentlik, LLP (57) ABSTRACT

A cervical biopsy instrument comprises a shaft defining a longitudinal axis and having a proximal end and a distal end; an arm extending laterally from the shaft; a cutting portion of cutting wire being supported at an outer end by the arm and being inclined relative to the longitudinal axis; and means for adjusting and setting the inclination and/or length of the cutting portion. This enables a single instrument to deal effectively with differently-sized, shaped and positioned cervical lesions, while tailoring the profile of the excision to the lesion concerned.

In the embodiments described, two opposed arms support two cutting portions, requiring 180° of angular movement during excision as opposed to the 360° movement of the prior art. The arms are mounted on a carriage for longitudinal adjustment, and can be bent individually to vary their length and hence the width of cut, which may be asymmetric. A centering means such as a collar is provided to ensure accurate centering within patulous cervical canals.

42 Claims, 6 Drawing Sheets

SURGICAL BIOPSY INSTRUMENT

CROSS-REFERENCE TO RELATED APPLICATIONS

This application is a continuation of International Application No. PCT/GB00/00645, filed Feb. 23, 2000 and published in English under International Publication No. WO 00/49955 on Aug. 31, 2000, the entire disclosure of which is incorporated herein by reference.

BACKGROUND OF THE INVENTION

This invention relates to the surgical biopsy excision of tissues, particularly but not exclusively the excision of abnormal lining in the uterine cervix.

Cancer of the uterine cervix, or cervical cancer, usually progresses slowly over an extended period from the first appearance of pre-cancerous abnormalities. With today's sophisticated screening programs involving regular smear testing, colposcopy and so on, this gradual progression presents an opportunity for many patients entirely to avoid cervical cancer if they can benefit from preventative intervention. Even for those who do not, there is a good prognosis if the cancer is detected and treated early enough.

Before malignant cells are found, the tissues of the cervix go through changes in which abnormal cells begin to appear, initially on the epithelial tissue on the surface of the cervix. This precancerous condition is known as dysplasia or cervical intraepithelial neoplasia (CIN).

CIN does not directly infer cancer but refers to a spectrum of abnormality ranging from mild dysplasia, that may regress without intervention, to severe dysplasia that may extend to carcinoma-in-situ, the cancer initially being localised to the intraepithelial tissue or superficial layer of the cervix. If left untreated, the cancer cells will start to grow and spread more deeply into the cervix and to surrounding areas, necessitating hysterectomy at best and, of course, threatening the patient's life.

If left untreated, around 30% to 50% of CIN conditions may progress to invasive cancer. Clearly, detection and treatment of CIN is essential to avoid the possible development of cervical cancer.

CIN is a lesion of abnormal cells typically associated with the Human Papilloma Virus (HPV). When HPV is contracted, it infects the cells of the transformation zone of the cervix where the cells of the cervix actively divide and grow. As those cells grow and mature, they are pushed to the surface as new cells are produced and the older, outside cells die and are shed. When the virus infects the cells and then becomes active, abnormal cells begin to be produced in the transformation zone and a lesion develops in the epithelial tissue at the surface of the cervix.

Removal of the lesion is an effective treatment for CIN. Although HPV remains once the CIN lesion is removed, the rate of recurrence of CIN is quite low since the removal of the transformation zone eliminates the tissue most susceptible to CIN.

Lesioned or dysplastic cells may be removed by cauterisation, cryosurgery or laser surgery. Cauterisation uses heat, electricity or chemicals to burn the abnormal tissue off the cervix. Cryosurgery freezes the cells and laser surgery destroys the cells with a laser beam. Various specific techniques include cryocautery, cold coagulation, large loop excision of the transformation zone, diathermy, needle excision of the transformation zone, cold knife cone biopsy, laser ablation, laser cone and a combination of cutting diathermy cones.

A common cervical excision procedure employs loop electrosurgery, sometimes called the Loop Electrosurgical Excision Procedure or LEEP. LEEP uses a thin wire loop electrode connected to an electrosurgical generator that emits an electric current to cut away affected tissue. A low voltage and relatively high frequency electric current is emitted from the loop into the tissue cells in the immediate area of the loop wire. Consequently, the cells heat rapidly, generating steam that causes the cells to burst microscopically and thus divides the tissue as the wire moves through the tissue. The wire is typically swept across the projecting neck of the cervix, or ectocervix, thereby removing a thin annular slice of tissue.

Unlike most other treatment methods, particularly ablative methods such as laser surgery, LEEP allows the physician to have the excised specimen analysed by a pathology laboratory. This allows for more accurate assessment of the abnormal tissue, which will confirm either that the lesion has been completely removed with the biopsy sample or, if it has not, what further treatment may be necessary.

The entire LEEP procedure usually takes less than fifteen minutes and is generally very effective and well received by patients. However, LEEP has its complications.

Because LEEP utilises electric current, burns to the vagina and other surrounding tissue may occur; such injury will cause unnecessary discomfort during and after the procedure, and may substantially lengthen the patient's recovery period.

Another problem of inaccurate use of a loop electrode is that the sample of tissue obtained may vary in amount and definition. LEEP is particularly prone to producing fragmented and burnt biopsy samples if it is necessary to make multiple passes of the loop, which reduces the accuracy of diagnosis. Multiple passes are particularly needed where, as is common, a lesion extends into the endocervical canal.

Incomplete removal of the lesion when excising the transformation zone is another, much larger potential risk, since this can only worsen the patient's long-term prognosis and will require further procedures to remove the remaining abnormal cells. This puts the patient through further unpleasant and emotionally draining treatment. The converse risk is the removal of too much tissue, which may result in cervical stenosis, an incompetent cervix, and/or sterility.

The underlying problem of LEEP is that the loop electrode is generally on the distal end of a long handle for which there is no guiding support in use. Once energised, the loop will instantly cut into and burn any tissue with which it comes into contact and so accurate positioning is critical both upon encountering the cervix and during excision of cervical tissue. Not only must the head of the instrument be placed exactly where it is needed before excision starts, but also the movement of the wire must be carefully controlled during its excising pass across the cervix. The lack of support makes it difficult for even an experienced physician to achieve an accurate cut; the problem is worse if the operating physician is inexperienced, particularly where visibility of the lesion is poor.

The inherent lack of stability of the loop electrode is exacerbated because the electrode itself can move in relation to the handle under the influence of drag as the electrode passes through the cervical tissue. This compounds the difficulty of knowing exactly where the electrode is at all times, and thus adds to the difficulty of producing an accurate cut.

Owing to the problems outlined above, there have been attempts to modify the standard loop cervical biopsy device.

The most notable modification is described in International Patent Application No. PCT/US95/01262 to Fischer, published as WO95/20922.

The Fischer instrument described in WO95/20922 has an elongated insulated body member with an endocervical portion at the distal end, a contact portion at the proximal end and a vaginal portion in between. An insulated stop arm extends at right angles to the body member from the junction of the endocervical and vaginal portions. A wire electrode extends diagonally between the stop arm and the endocervical portion.

The Fischer instrument is sold by a US company, Apple Medical Corporation. It has come to be known among physicians as the Fischer cone biopsy device or simply as the Fischer cone, which term will be used hereafter for brevity.

In use, the Fischer cone is connected by means of the contact portion to an electrosurgical generator such as a blend cutting diathermy machine. The instrument is then inserted into the cervix through the vaginal canal, the vaginal canal being held open by a duckbill speculum as is well known in the art. The endocervical portion is aimed into the cervical canal to gain support for the distal end of the instrument, whereupon the wire is energised through the contact portion and conductor means within the insulated body.

When the energised wire contacts the cervical tissue at the ectocervix, a current passes through the wire into the patient to return through an electrode attached to a convenient part of the patient's body. This current heats the tissue cells adjacent the wire until they burst. The wire is then advanced through the cervix, separating the cervical tissue, with the endocervical portion extending further into the cervical canal until the stop arm touches the ectocervix. When this position is reached, the instrument is turned one full revolution (360°) about its longitudinal axis to cut a conical tissue specimen from the transformation zone. The current is then turned off and the cut specimen is withdrawn with the instrument from the vaginal canal.

The endocervical portion extending into the cervical canal acts as a pivot about which the Fischer cone is turned during the cutting operation, the pivot rotatably supporting the distal end of the instrument. Also, the arm abutting the ectocervix acts to determine the depth of cut during the cutting operation. Optionally, a bi-directional arm seats the instrument on opposite sides of the cervical canal to increase stability during rotation. To an extent, therefore, the Fischer cone allows the excision to be performed partially by feel.

The accuracy of the Fischer cone is improved further over the loop electrode because the arm holds the diagonal electrode taut and straight throughout the procedure, and because the electrode itself is as short as possible.

Whilst the improved stability, ease of use and hence accuracy afforded by the Fischer cone have been well received among physicians, the Fischer cone also has its drawbacks.

One problem is that every abnormal cervix is unique in its size and shape and in the position, depth and extent of the lesion. The only way of adapting the Fischer cone to these variations is to provide a preordained range of instruments that differ in the length and angle of the diagonal electrode. This leaves the physician to select an appropriate one of the range, hoping that the patient and the necessary biopsy sample accord with one of the available instruments.

Of course, it rarely happens that the chosen instrument exactly suits the cervix and lesion in question. Lesions are rarely evenly distributed around the transformation zone and, indeed, may be deeper in some areas compared to others. Consequently, when using the Fischer cone, if more tissue must be removed from one area of the cervix compared to another, the less affected area will be subjected to unnecessary damage that may ultimately cause the same problems encountered with LEEP. The only way around this is to make a partial cut by turning the instrument through less than 360°, or locally to reduce the depth of cut by partially withdrawing the instrument during the cutting sweep. Neither technique uses the Fischer cone to its best advantage.

A further drawback of the Fischer cone is the need to turn the instrument through a full 360° when it is desired to make a full conical excision. This introduces the possibility of error because the physician must change his or her grip on the instrument during the excision movement: the physician's wrist cannot turn through 360°. The possibility of error is heightened if the cervical canal is wider than the endocervical portion of the instrument, as is common in so-called patulous or stretched-open cervices: the cervical canal cannot then receive the endocervical portion snugly enough to create a fixed pivot point and hence cannot center the endocervical portion accurately.

The range of just five Fischer cone configurations currently on sale cannot possibly cater for all situations. The result of this is that use of the Fischer cone may still require the physician to apply considerable skill by controlling the movement of the instrument in a particular way during excision.

Whilst skill will always be required successfully to perform a cervical biopsy procedure, there is a need to improve the accuracy, efficacy and ease of use of existing instruments. The present invention has arisen from this background and has been developed with that need in mind.

SUMMARY OF THE INVENTION

From one aspect, the invention resides in a cervical biopsy instrument comprising:

a shaft defining a longitudinal axis and having a proximal end and a distal end;

an arm extending laterally from the shaft;

a cutting wire capable of cutting tissue when current is supplied to the wire in use through conductor means in the shaft, a cutting portion of the cutting wire being supported at an outer end by the arm and being inclined relative to the longitudinal axis such that the cutting portion of the wire converges with the longitudinal axis moving from the arm towards the distal end; and means for adjusting and setting the inclination and/or length of the cutting portion.

The facility for adjusting and setting the inclination and/or length of the cutting portion confers adaptability on the instrument of this invention. It enables a single instrument to deal with differently-sized, shaped and positioned cervical lesions in a manner that is clinically effective but minimally invasive. Put another way, the invention helps a physician to strike the difficult balance between excising too little, potentially endangering the patient's life through failure to halt the onset or progress of cervical cancer, and excising too much, potentially leading to an incompetent cervix and the end of the patient's reproductive capacity.

It is preferred that the inclination and/or length of the cutting portion are steplessly adjustable to allow the instrument to be tailored precisely as the physician may require.

Whilst it is preferred that the cutting portion extends from the outer end supported by the arm to an inner end supported by the shaft at or near the distal end, the inner end of the cutting portion need not be supported directly by the shaft but could be supported by some other support structure that is supported in turn by the shaft.

In particularly preferred embodiments, a plurality of arms extend laterally from and are angularly spaced about the shaft, each arm supporting a respective cutting portion at an inclination relative to said longitudinal axis such that the cutting portions converge with the longitudinal axis approaching the distal end. More preferably, at least first and second arms are opposed about the shaft so that the cutting portions of cutting wire supported by those arms are substantially coplanar.

By providing more than one arm on the instrument of the invention and by disposing those arms around the shaft in, for example, a diametrically-opposed, 180°-spaced arrangement, the physician need not turn the instrument through a full 360° in order to excise a full conical tissue specimen. Instead, a 180° turn will suffice and an even smaller turn will suffice if more than two arms are used. In general, the less angular movement the physician needs to effect, the better the chance of a consistent and correct position and depth of cut. Nevertheless, two arms are deemed sufficient for the purposes of the invention and are preferred to a greater number of arms.

Of course, a physician need not necessarily cut through a full 360°: preferred embodiments of the invention provide for adjustment of the instrument to avoid cutting, or to reduce the depth of cut, on one side of the cervix. For example, it is contemplated that the or each arm can be variable in length and, if there are two or more variable-length arms, that the length of one arm can be adjusted independently of the or each other arm. Also, it is always up to the physician how far he or she wishes to turn the instrument and therefore how much he or she wishes to cut.

The provision of more than one arm also aids centering of the instrument within the cervical opening both upon insertion of the instrument and during excision of tissue. The relative symmetry of the instrument, and the closer equality of drag forces experienced on both sides of the longitudinal axis during turning, lends a degree of self-centering that is absent in the asymmetric prior art instruments.

It is further preferred that the or each arm is movable during adjustment in a direction parallel to the longitudinal axis with respect to the distal end of the shaft. To that end, the or each arm may be mounted on a carriage mounted in turn to the shaft for movement along the shaft. For simplicity, this longitudinal movement of the or each arm is preferably a sliding movement that keeps the arms in fixed angular relation to the shaft.

Where the position of the inner end of the cutting portion is fixed with respect to the distal end of the shaft, moving the or each arm in this way without changing its length will tend to lengthen or shorten the cutting portion and to alter its angle of inclination with respect to the longitudinal axis. This is one way of adjusting the instrument to excise an appropriate part of the cervix.

To aid correct positioning, the shaft may have graduation means visible during adjustment to indicate the position of the or each arm with respect to the distal end of the shaft. To keep the correct position, means are suitably provided for locking the carriage to prevent movement of the carriage with respect to the shaft.

In another way of adjusting the instrument to excise an appropriate part of the cervix and as mentioned above, the or each arm is variable in length with respect to the longitudinal axis to vary the distance of the outer end of the associated cutting portion from the longitudinal axis. Whilst many variously complex ways to achieve this will be apparent to those skilled in the art once given the inventive concept, it is preferred in this invention simply that the or each arm is plastically deformable to the extent that it can be bent before use to adjust its shape and length and will then hold that shape and length in normal use of the instrument.

Where there are two or more variable-length arms and the length of one arm can be adjusted independently of the or each other arm, an asymmetric cut can be achieved by a simple turn of 180° or less. This can be of singular importance where, as is common, the lesion is asymmetric or the cervix is distorted and so it is desirable not to excise tissue to the same depth around the entire cervix.

Again, altering the length of the or each arm in this way without changing its longitudinal position with respect to the distal end will tend to lengthen or shorten the cutting portion and to alter its angle of inclination with respect to the longitudinal axis.

In practice, the different forms of adjustment provided by preferred embodiments of the invention can be used together with great flexibility. In this way, a physician can tailor the instrument to deal with the particular cervix and lesion concerned, without having to use one of a range of different instruments—none of which may be quite right for the task in question.

If the cutting portion is shortened by either of the above means of adjustment, retractor means are advantageously provided to retract excess cutting wire and thereby to keep the cutting portion taut and straight. The retracted cutting wire can be held in storage means, to be paid out if the cutting portion is lengthened. For compactness and robustness, the retractor means and the storage means are preferably within the shaft although it is conceivable that these means could be exposed. It is further preferred that the cutting portion is fixed at its outer end to the arm and that its inner end is supported by the shaft in a manner that allows the cutting wire to move under the influence of the retractor means as the cutting portion is varied in length. This simplifies the construction of the or each arm. It would, however, be possible to reverse the arrangement such that the cutting portion is fixed at its inner end to the shaft and is supported at its outer end by the or each arm in a manner that allows the cutting wire to move as the cutting portion is varied in length.

In any arrangement, it is highly advantageous that the retractor means maintains tension on the cutting portions after adjustment. Conveniently, the retractor means comprises spring means acting in tension. There may be first and second spring means, the first spring means being disposed distally with respect to the second spring means and the spring means being offset longitudinally from each other to an extent necessary to permit their maximum extension in use. In that event, there is room for both spring means even when they are within a tubular shaft portion and have an aggregate diameter greater than the internal diameter of that shaft portion.

In an alternative arrangement, the first and second spring means are at longitudinally corresponding positions beside each other. In that event, the first and second spring means are preferably segregated from each other to ensure that each can operate without interference from the other. An elegant development employs common spring means acting on both of the first and second wires to tension and retract the cutting portions. The partition between first and second wires suitably has an opening through which the common spring means extends.

As the opening of a stretched or patulous cervical canal may be wider than the shaft, a centering means is preferably provided that is movable along the shaft in a direction parallel to the longitudinal axis, the centering means being advanced towards the distal end of the shaft to engage, in use, within the cervical canal. To cater for different sizes of cervical canal, the centering means preferably defines a cervix-engaging surface that tapers towards the distal end of the shaft. In a simple arrangement that achieves this objective, the centering means is a frusto-conical collar around the shaft that can be advanced along the shaft when it is desired effectively to widen the shaft to fit a patulous cervix.

This aspect of the invention has independent applicability and therefore the invention may also be expressed as a cervical biopsy instrument comprising a shaft defining a longitudinal axis and having a proximal end and a distal end, a distal end portion being received in use within a cervical canal to form a pivot for an angular excision movement about the longitudinal axis, the instrument further including centering means positionable at the distal end portion to center the shaft within a cervical canal that is wider than a transverse diameter of the distal end portion.

To avoid interference with the insertion of the distal end portion into a normal cervix, the centering means preferably has a parked position disposed proximally with respect to the or each arm. The centering means can then be advanced into a cervix-engaging position disposed distally with respect to the or each arm.

Where the centering means is a collar around the shaft, the collar can resiliently grip the shaft or the centering means and the shaft can have complementary threads by which the centering means can be moved longitudinally with respect to the shaft.

From another aspect, the invention in its broadest sense does not require adjustability of the angle and length of the cutting portion but instead resides in a cervical biopsy instrument comprising:

a shaft defining a longitudinal axis and having a proximal end and a distal end;

a plurality of arms extending laterally from and being angularly spaced about the shaft, each arm supporting a respective cutting portion of cutting wire being capable of cutting tissue when current is supplied to the wire in use through conductor means in the shaft;

each cutting portion being held by a respective arm at an inclination relative to said longitudinal axis, said inclination being such that the cutting portions converge with the longitudinal axis approaching the distal end.

As before, it is preferred that first and second arms are diametrically opposed about the shaft so that the cutting portions of cutting wire supported by those arms are substantially coplanar.

BRIEF DESCRIPTION OF THE DRAWINGS

In order that this invention can be more readily understood, reference will now be made by way of example to the accompanying drawings in which.

DETAILED DESCRIPTION OF THE INVENTION

Referring firstly to FIGS. 1 to 4 of the drawings, an instrument (1) in accordance with a first embodiment of the invention comprises a straight hollow tubular shaft (2) of circular cross-section, made of any suitably sturdy electrically insulated or insulating material. The shaft is not drawn to scale but in reality would have an exemplary diameter of about 5 mm and a length of about 120 mm.

Figure 1:
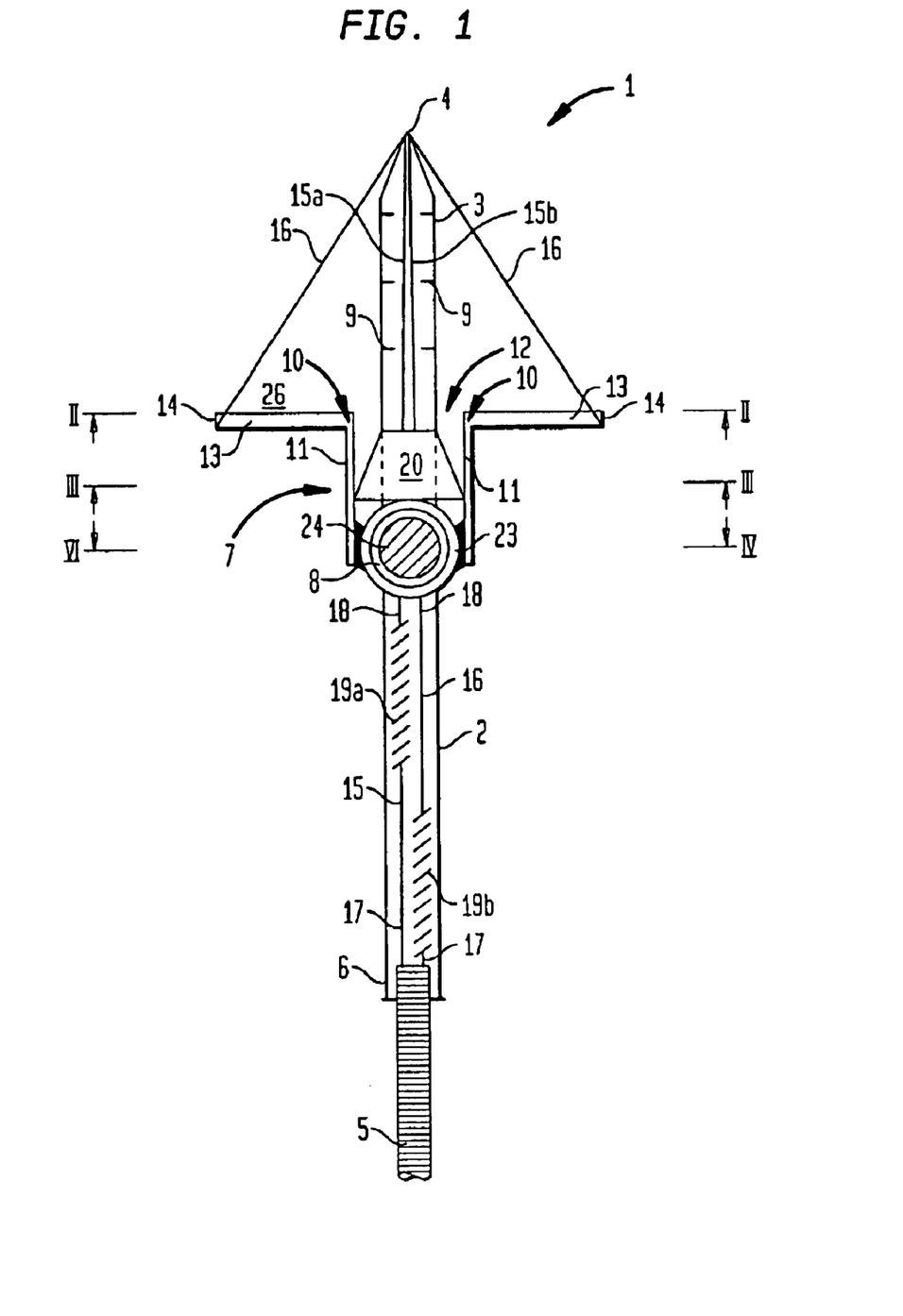
FIG. 1 is a schematic sectional elevation of a first embodiment of the invention with the cutting portions near to their maximum length, the carriage supporting the arms being remote from the distal end and being moderately extended, and a centering means in a parked position.

The shaft has a distal end portion (3) of a material that can withstand the high temperatures experienced during excision. The distal end portion tapers at its end to terminate at the distal end in a point defining a narrow central hole (4) whose purpose will be explained. Otherwise, the walls of the shaft are generally parallel and symmetrical about a central longitudinal axis of the shaft.

An electrode (5) fits snugly within the proximal end (6) of the tubular shaft. The exposed outer or proximal end of the electrode (5) can be conductively connected to a blend cutting diathermy machine of known type, for example as is used with the Fischer cone.

An annular carriage (7) is slidable longitudinally in stepless manner along the outside of the shaft (2). A locking means (8) locks the carriage (7) to the shaft (2) in a desired longitudinal position, using a mechanism that will be explained below with reference to FIG. 4. Graduations (9) marked externally on the distal portion of the shaft (3), in the example shown at 10 mm intervals from the distal end, allow the user readily to gauge the longitudinal position of the carriage (7) with respect to the distal end.

The carriage (7) supports two mutually-opposed arms (10) that extend laterally about the shaft (2) in a diametrically-opposed, 180°-spaced arrangement when viewed from an end of the shaft (2). Each arm (10) has an inner portion (11) extending distally from the carriage (7) a short distance, for example 10 mm, substantially parallel to the longitudinal axis of the shaft (2). The inner portions (11)

are spaced from the shaft to define a recess (12) around the shaft (2), whose purpose will be explained, the recess (12) being, for example, about 10 mm wide. Each arm (10) also has an outer portion (13) extending orthogonally outwardly with respect to the longitudinal axis from the distal end of the inner portion (11), the outer portion (13) terminating in a free end (14).

Figure 2:
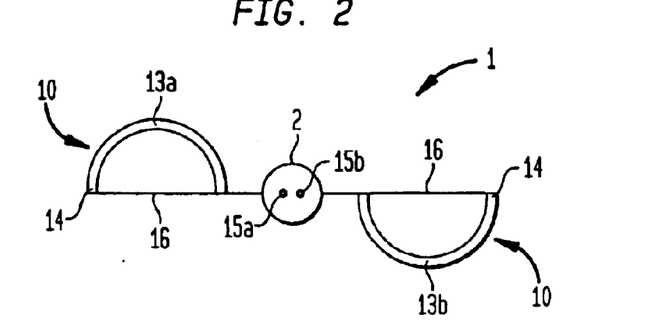
FIG. 2 is a cross-sectional end or plan view on line II—II of FIG. 1, showing the shape of the arms.

The outer portions (13) of the arms (10) appear straight in the side view of FIG. 1 but as will be clear from the sectional view of FIG. 2, the outer portions (13) are oppositely curved in end or plan view. The curvature is opposed in the sense that one outer portion (13a) is curved to one side of a line joining the free ends (14) of the outer portions (13) and extending through inner portions of the arms (11) and the central longitudinal axis of the shaft (2), and the other outer portion (13b) is curved to the other side of that line.

The curvature of the outer portions of the arms (13) is semi-circular in the illustration, but may be varied at will. In this respect, it will be noted that the cross-section of each outer portion (13) is somewhat flattened so that the thickness of the outer portions (13) is greater when viewed from the side than it is in plan or end view. This facilitates a useful optional feature of the invention, which is that the outer portions of the arms (13) can be bent in plan or end view to vary and set their length. The curvature of the outer portions (13) is variable from straighter, to lengthen the arms (10), to more acutely curved, to shorten the arms (10).

For example, the outer portions (13) may each be 30 mm long around the curve, meaning that the maximum length of each arm (10), when the outer portion is straightened, is 30 mm from the distal end of the inner portion (11). A typical length when the arm (10) is curved would be say 20 mm, within a possible range of perhaps 5 mm to 30 mm.

To enable this feature, the outer portions of the arms (13) are made of a plastically-deformable and preferably manually-bendable material such as thick insulated wire that will not be fatigued by repeated bending and that can retain its set during the loading of normal use. The inner portions of the arms (11) are made of a relatively rigid insulated wire that will not bend as the outer portions are bent.

First and second wires (15a, 15b) are conductively connected at spaced locations to the distal or inner end of the electrode (5) and extend distally from the electrode within the hollow shaft (2), lying beside each other and extending to the tapered distal end (3). The wires (15) taper towards each other as they approach the distal end (3), being supported at the distal end by the rim of the hole (4) whose diameter is smaller than the spacing between the wires (15) where they are connected to the electrode (5).

The wires (15) exit the shaft (2) through the hole (4) at the distal end (3), from where the wires (15) then sweep back oppositely, proximally and outwardly, defining straight cutting portions (16) that are inclined relative to the longitudinal axis of the shaft (2). Each cutting portion (16) extends to, and is anchored at, the free end (14) of the outer portion of a respective arm (13). The cutting portions (16) are therefore coplanar with each other and with the distal end of the shaft (3) and define a generally triangular cutting head (26) about the shaft (2).

Within the shaft (2), the first and second wires (15) comprise respective proximal wire portions (17) and distal wire portions (18) joined by respective coil springs (19). The springs (19) act in tension at all times to keep the wires (15) and hence the cutting portions (16) taut and straight however the arms (10) may be adjusted. When adjustment of the arms (10) makes the cutting portions (16) shorter, the excess wire (15) is retracted into the shaft (2) by the tension of the springs (19). By shortening under their own tension, the springs (19) also store the excess wire (15) within the shaft (2). Conversely, when adjustment of the arms (10) makes the cutting portions (16) longer, the springs (19) lengthen to release or pay out stored wire (15) to the cutting portions (16).

Each of the proximal wire portions (17) is conductively connected at a proximal end to the electrode (5) and at a distal end to a respective spring (19). Each of the distal wire portions (18) is conductively connected at a proximal end to a respective spring (19) and extends distally from there to the distal end of the shaft (3). The springs (19) conduct current from the electrode (5) to the distal wire portions (18) for supply to the cutting portions (16) in use and so, for the purposes of this description, the springs (19) can be taken to be part of the first and second wires (15).

It will be noted that the spring of the first wire (19a) is located near the middle of the shaft (2) and hence distally with respect to the spring of the second wire (19b), which spring is located near the proximal end of the shaft (2). This longitudinally offset spring arrangement is advantageous because it allows the shaft (2) to accommodate two springs (19) whose aggregate diameter is potentially wider than the internal diameter of the shaft (2). The degree of offset between the springs (19) is such that each can extend to its maximum length, which is when the cutting portions (16) are at their longest, without interfering with the other spring (19) also at its maximum length.

Figure 3:
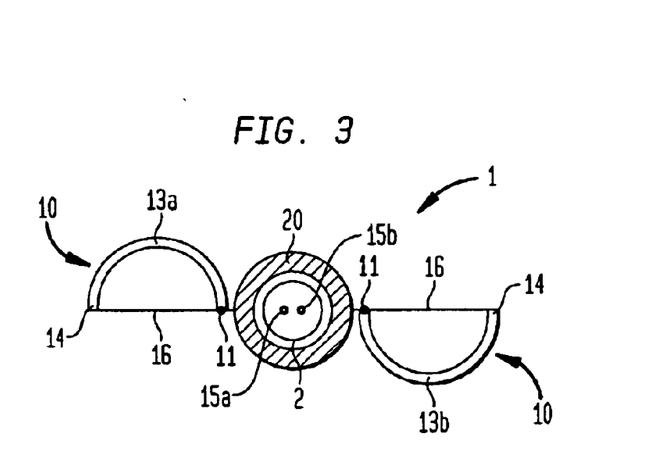
FIG. 3 is a cross-sectional end or plan view on line III—III of FIG. 1, showing the disposition of the centering means in the form of a collar around the shaft.

In the preferred embodiments illustrated, a centering means takes the form of a collar (20) made of any suitable material such as rubber, plastics or a combination thereof. The collar (20) fits snugly around the shaft (2), having a central longitudinal bore to match the outer diameter of the shaft and thus having a diameter of about 5 mm in the example shown. The collar (20) is about 10 mm in length in the example shown, and tapers from a proximal base about 10 mm wide to a distal tip that is barely wider than the shaft (2). The tapered frusto-conical surface of the collar (20) is shaped to fit snugly within the openings of patulous cervical canals of various diameters.

It will be noted that the collar (20) is dimensioned to rest as illustrated in a parked position within the aforementioned recess (12) between the inner portions of the arms (11) and hence proximally behind the outer portions of the arms (13). There, the collar (20) will not interfere with insertion of the instrument (1) into a normal cervix or a tightly-closed, i.e. stenosed cervix up to a cutting depth at which the outer portions of the arms (13) bear against the ectocervix (21). In these instances, the shaft (2) is received snugly enough within the cervical canal (22) to center itself accurately. However, when required to aid centering within a patulous cervix, the collar (20) is advanced towards the distal end of the shaft (3), moving out of the parked position and into a cervix-engaging position distally in front of the outer portions of the arms (13). In that position, the collar (20) will engage snugly within the opening of the cervical canal (22) when the cutting portions (16) reach their cutting depth in use and the outer portions of the arms (13) bear against the ectocervix (21), ready for the instrument (1) to be pivoted in an excision movement.

In the embodiment shown, the fit between collar (20) and shaft (2) is such that the collar (20) can be moved comfortably by the user's fingers along the shaft (2) but without being loose, the preferred resilience of the collar (20) gripping the shaft (2) in any position to prevent slippage of the collar (20) under the normal longitudinal loads of use. Other arrangements are possible, as will be explained at the end of this description.

The aforementioned graduations (9) marked on the distal portion of the shaft (3) have the primary purpose of aiding setting of the longitudinal position of the arms (10), but it will be noted that the graduations (9) also allow the user readily to gauge the longitudinal position of the collar (20) with respect to the distal end of the shaft (3).

Figure 4:
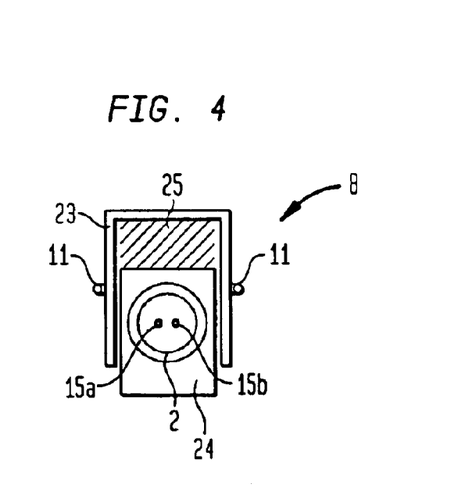
FIG. 4 is a cross-sectional end or plan view on line IV—IV of FIG. 1, showing the internal features of the locking means.

Returning now to the locking means (8), this could be made of any suitable shape and of any suitable material, and can employ any of a variety of mechanisms. A simple and therefore preferred locking arrangement is illustrated and comprises a circular-section tubular housing (23) that supports the arms (10) and therefore doubles as the main structural part of the carriage (7).

As best shown in the sectional view of FIG. 4, the central axis of the housing (23) is oriented orthogonally with respect to the longitudinal axis of the shaft (2). The housing (23) has a blind end, an open end and aligned holes penetrating its cylindrical wall to admit the shaft (2) as a sliding fit in said orthogonal orientation. The housing (23) further contains a plunger (24) in the form of a short snug-fitting piece of round bar aligned with the central axis of the housing (23). The plunger (24) is penetrated by a transverse bore that is orthogonal to the central axis of the housing (23) and can be aligned with the holes in the housing, the bore similarly receiving the shaft (2) as a sliding fit when so aligned. The outer end of the plunger (24) extends slightly outside the housing (23).

A coil spring (25) within the housing (23) acts in compression between the blind end of the housing and the inner end of the plunger (24), biasing the bore in the plunger (24) out of alignment with the holes in the housing (23) and so applying friction to the shaft (2) where the housing (23) and the plunger (24) are in contact with the shaft (2). This friction locks the housing (23) with respect to the shaft (2), to the extent that longitudinal or angular movement of the arms (10) with respect to the shaft (2) is prevented under the normal loading of use. However, when it is desired to move the arms (10) longitudinally during adjustment of the instrument (1) before use, it will be noted that the outer end of the plunger (24) presents a button surface that can be depressed against the biasing force of the spring (25) to align the bore of the plunger (24) with the holes of the housing (23) and thus to release the housing (23) for easy sliding movement along the shaft (2). Freeing the mechanism in this way is a simple and wholly intuitive movement for the user wishing to move the carriage (7).

The shape of the triangular cutting head (26) and the extent to which the instrument (1) is turned in use about the longitudinal axis of the shaft (2) defines the shape and extent of the cervical excision. The shape of the triangle (26) is determined by the longitudinal position of the carriage (7) and hence of the arms (10) with respect to the distal end (3), and also by the shape and hence the length of the arms (10) themselves. For example, moving the carriage (7) proximally along the shaft (2) will make the excision biopsy longer and deeper. In another mode of adjustment, straightening or increasing the curvature of the outer portions of the arms (13) will respectively widen or narrow the base of the excision biopsy. Such manoeuvres allow excision biopsies to be taken from even the most distorted cervices.

Figure 5:
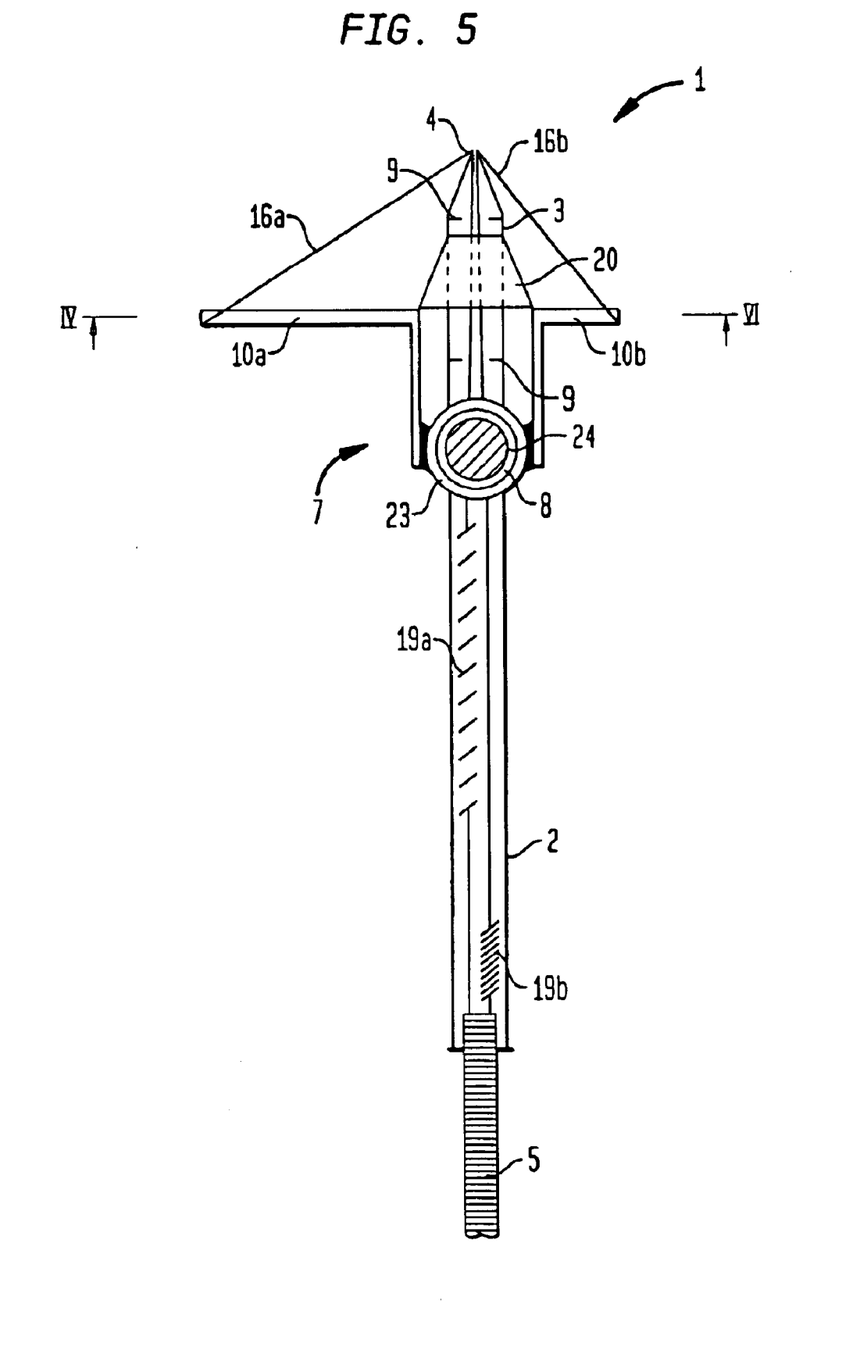
FIG. 5 is a schematic sectional elevation corresponding to FIG. 1 but showing the first embodiment adjusted for use with one arm having been extended further, the other arm having been shortened, the carriage having been set closer to the distal end and a centering means having been advanced into a cervix-engaging position.
Figure 6:
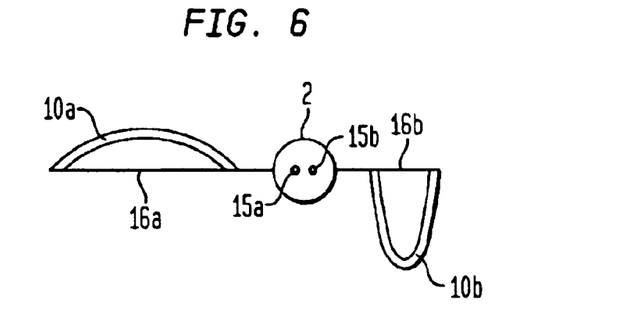
FIG. 6 is a cross-sectional end or plan view on line VI—VI of FIG. 5 that corresponds to FIG. 2 but shows the shape of the arms as adjusted for use.
Figure 7:
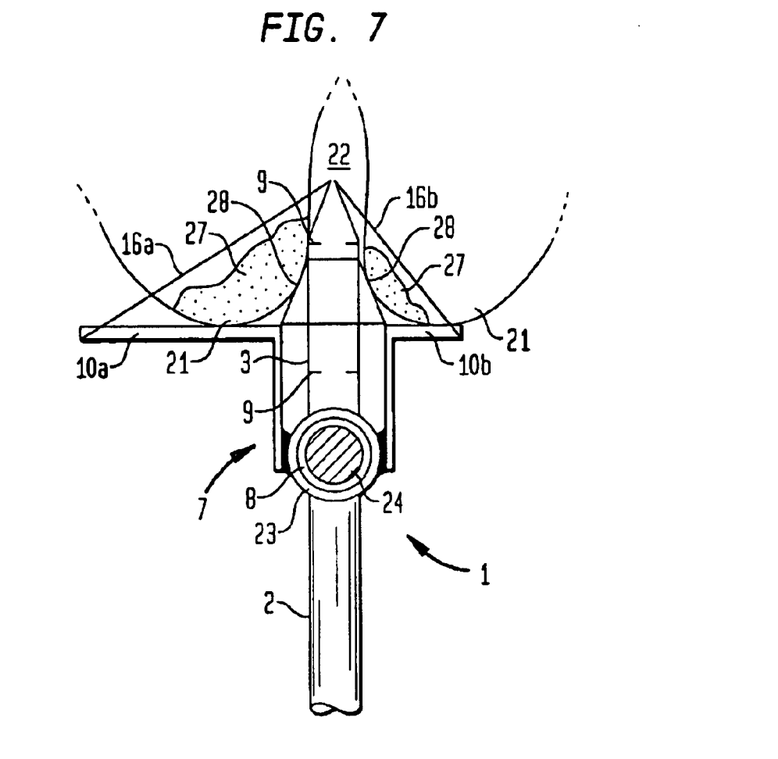
FIG. 7 is a sectional side view of the first embodiment in use in cervical biopsy excision performed on a patulous cervix.

FIGS. 5, 6 and 7 are intended to illustrate how the instrument of FIGS. 1 to 4 might be adjusted in use and the illustrative situation contemplated therein is deliberately unusual but not impossible. In this situation, the cervix (22) shown in FIG. 7 is patulous to the extent that the endocervical opening is wider than the distal end portion (3) of the instrument (1), and the cervix (22) bears a heavily asymmetric lesion (27) requiring a wider cut to one side of the cervical canal (22) and a narrower cut to the other side. Nevertheless, the lesion (27) does not extend far into cervical canal (22) and so a relatively shallow cut is called for.

With this difficult cervical configuration in mind, the physician has adjusted the instrument (1) as best shown in FIGS. 5 and 6. Firstly, it will be noted that one arm (10a) has been extended and the other arm (10b) has been shortened to reflect the asymmetry of the lesion (27). The carriage (7) has been set closer to the distal end (3) to take a shallower cut, and the centering collar (20) has been advanced into a cervix-engaging position intermediate its parked position and the distal end of the shaft (3).

FIG. 7 shows the interaction of the instrument (1) as adjusted in FIGS. 5 and 6 with the cervix (22) that the adjustment was intended to suit. The instrument (1) shown in FIG. 7 has been connected to an electrosurgical generator (not shown) and has been inserted into the cervix (22) through the vaginal canal, the vaginal canal being held open by a suitable speculum (not shown). The angular orientation of the instrument (1) about the longitudinal axis of the shaft (2) has been selected and controlled by the physician to bring the appropriate cutting portion (16) (i.e. that supported by the extended arm) into position to cut the lesion (27).

The instrument (1) is shown in FIG. 7 before being turned through 180° about its longitudinal axis to excise the lesion (27), but after the distal end portion (3) has been inserted into the cervical canal (22) and the arms (10) have contacted the ectocervix (21). The arms (10) thus prevent deeper insertion and signal to the physician by feel that the correct depth of insertion has been achieved. It is to be noted that the cutting portions (16) were energised since first contact with the endocervix (28) and so, in FIG. 7, they have already cut through the ectocervix (21) the cutting depth predetermined by the adjusted disposition of the cutting portions (16).

It will be evident from FIG. 7 that the collar (20) has done its job by filling the patulous cervical canal (22) and so providing a reliable pivot point about which the instrument (1) can be turned during the forthcoming cutting operation. Both cutting portions (16) have gone in deeply enough to excise all of the CIN tissue that forms the lesion (27), but the cutting portion (16a) supported by the longer arm (10a) will produce a cut of greater radius during the cutting operation than will be cut by the other cutting portion (16b). In this way, all of the asymmetric lesion (27) will be removed but minimal damage will be caused to relatively unaffected areas of the cervix (22).

Figure 8:
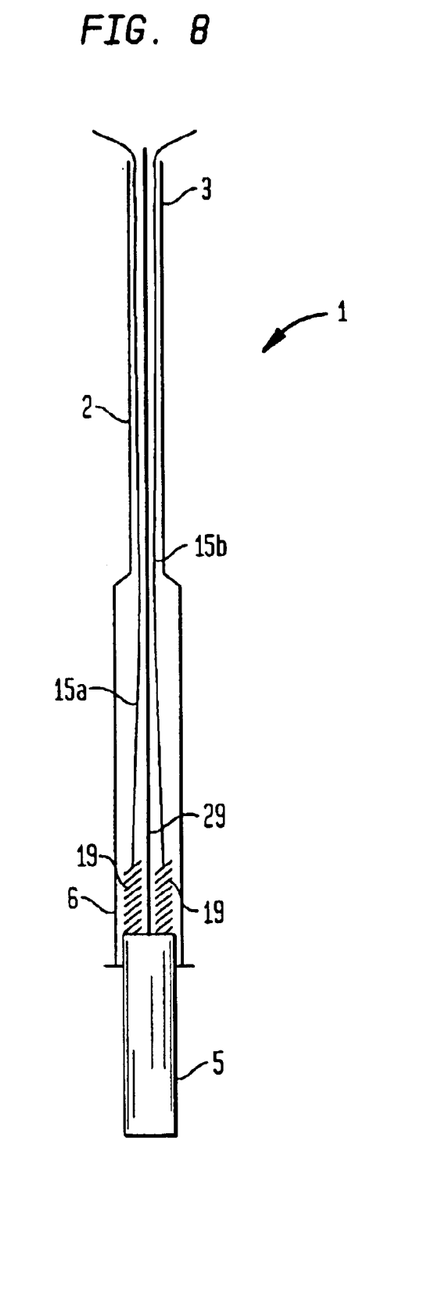
FIG. 8 is a partial schematic sectional view showing details of a second embodiment of the invention that employs a different retractor spring arrangement.

Referring now to FIG. 8, the second embodiment illustrated therein is similar in principle to the first embodiment. To that extent, like numerals are used for like parts and the drawing is abbreviated to show only the internal features of the tubular shaft (2) that are different to the first embodiment. It will be seen that the shaft is divided by a central longitudinal partition (29) into two compartments that extend beside each other from the electrode (5) at the proximal end (6) all the way to the distal end (3). However, it would be possible for the partition (29) to be shortened, interrupted or dispensed with. Otherwise, the distal portion of the shaft (3) is very much narrower than the proximal portion (6), being just wide enough internally to allow the first and second wires (15) to pass through to the distal end (3) within their respective compartments. The proximal portion (6) is much wider to allow free movement of springs (19) disposed beside each other in their respective compartments, effectively in parallel to one another. The springs (19) are anchored at their proximal ends directly to the distal end of the electrode (5).

Figure 9:
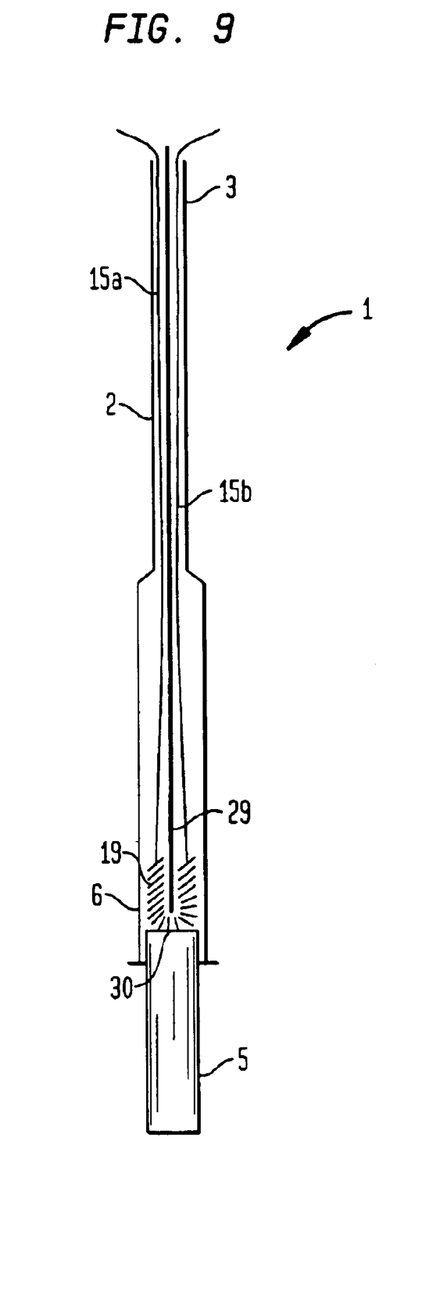
FIG. 9 is a partial schematic sectional detail view of a modification of the second embodiment that employs a common retractor spring acting on both cutting portions.

Another spring arrangement for the second embodiment is shown in FIG. 9. Instead of having two springs (19), one in each compartment, there is just one spring (19) that serves both compartments. The spring (19) is conductively connected to the electrode (5) at its mid point (30), and its ends are conductively connected to the respective wires (15a, 15b). To enable this, the ends of the spring (19) extend into the respective compartments through an opening in the proximal end of the partition (29).

Figure 10:
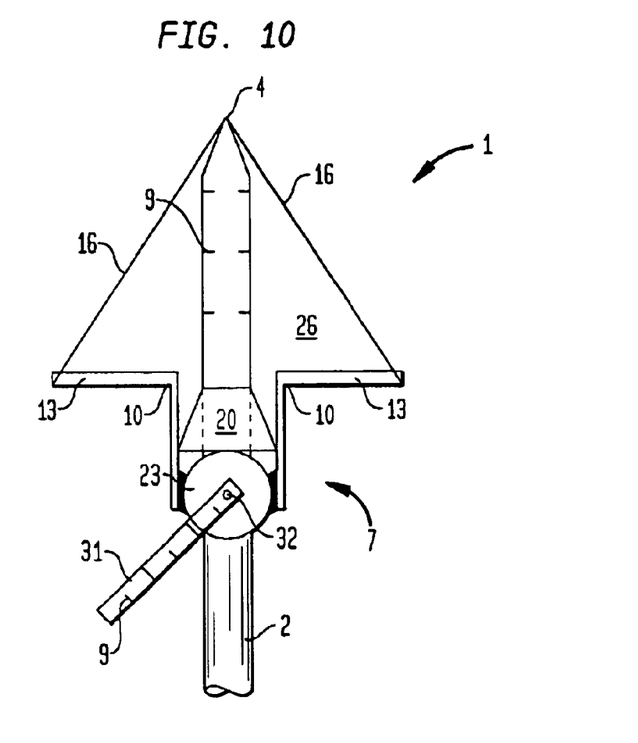
FIG. 10 is a schematic sectional elevation that broadly corresponds to FIG. 1 but shows a modification of the first embodiment in the form of a ruler to gauge the length of the arms.

An optional addition to either embodiment is illustrated in FIG. 10 in relation to the first embodiment. This addition is a ruler (31) providing graduations (9) to assist in setting the length of the arms (10). In the illustrated embodiment, the ruler (31) is a flat narrow strip about 30 mm long, one end of which is pivotally attached to the carriage (7) by a pin (32) extending through the ruler (31) and into the blind end of the housing (23) of the locking means (8). When not in use, the ruler (31) lies against and parallel to the shaft (2) with the free end of the ruler pointing proximally. When moved angularly in either direction around its pivot (32), the ruler (31) can be oriented in parallel with the outer portions of the arms (13) to allow direct and exact measurement of the cutting radius of each arm (10). It is also possible that the arms (10) themselves could be graduated to give the desired radius.

Figure 11:
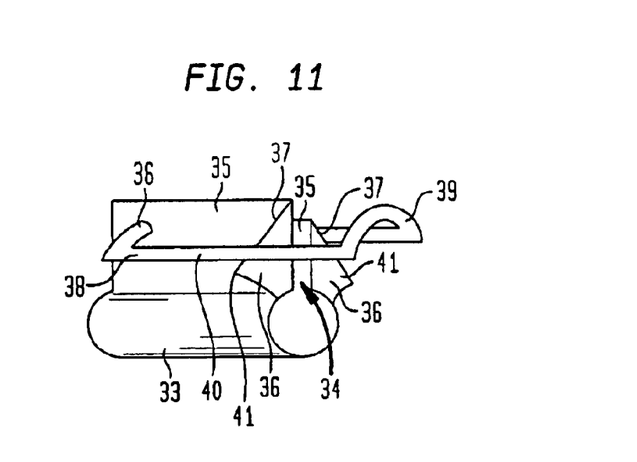
FIG. 11 is a schematic perspective view of an alternative locking means for the carriage.

Another locking means explained now by way of example is illustrated in FIG. 11. The locking means (8) therein comprises a C-section part-cylindrical sleeve (33) that partially surrounds the shaft (not shown), leaving a longitudinal slit (34) defined between parallel outwardly-extending oblong flaps that in use are parallel to the longitudinal axis of the shaft. Each flap (35) contains an offset hole (36) near one end and terminates in a triangular radially-extending wing (36) at the other end, the wings of the respective flaps (36) facing away from each other. An edge of each wing (36) defines a ramp (37) that tapers towards the flap (35) moving away from the sleeve (33).

A clip (38) in the form of a generally oblong piece of strong spring wire is pivotally received at one end by the holes (36) so that its long sides can engage the ramps (37) of the opposed wings (36). When the free end of the clip (39) is pressed towards the sleeve (33) in use, the long sides of the clip (40) move up the ramps (37), pressing the triangular wings (36) towards each other and thus tightening the sleeve (33) about the shaft (2). The sleeve (33) is tightened until the long sides (40) engage with respective notches (41) at the end of the ramps (37) to secure the clip (38) with the sleeve (33) locked to the shaft (2). To release the grip, the clip (38) is pulled in a reverse direction to disengage from the notches (41).

As before, this locking means (8) is preferably integral with or synonymous with the carriage (7). For example, the arms (10) may be attached directly to the sleeve (33) in a manner analogous to the direct attachment of the arms (10) to the housing (23) in the first embodiment.

Many variations are possible without departing from the inventive concept. For example, it is possible for the or each spring (19) to be formed integrally with the wires (15) inside the shaft (2), and it is not essential that the or each spring (19) is a coil spring.

In an alternative arrangement for advancing the centering collar (20) into a cervix-engaging position, the external surface of the distal portion of the shaft (3) and the bore of the collar (20) have complementary threads so that the collar (20) can be screwed along the shaft (20) simply by turning it about the shaft (2). The pitch of the thread can be selected so that the collar (20) will stay put under the normal conditions of use, once screwed into the desired cervix-engaging position.

To recap, the excision instrument of the present invention has numerous advantages. It is simple and quick to use. The instrument described can take out any shape of CIN of any depth up to 30 mm and any diameter up to more than 60 mm. Excision biopsies could be taken even from the smallest cervices because the tapering distal end allows excision of CIN to be taken even from stenosed (narrowed) cervical canals.

The arms (10) can work independently of each other so that, for example, half the excised CIN could be of 30 mm radius while the other half could be of 10 mm radius. This facility allows CIN excision to be taken from completely distorted cervices, which are quite commonly encountered. In all cases, there is better exposure of the cervix, and blood loss is usually minimal.

The collar (20) can be moved towards the distal end of the shaft (3) when used in patulous (stretched open) cervices, thus filling the cervical canal to control symmetrical CIN excision. For all cervices, the need to rotate the instrument through only 180° makes excision simple, and the ability to pre-set the height and the base of the triangular cutting head (26) produces a predictable mirror image of the piece of tissue that is to be excised.

By use of the invention, CIN excision could be taken under local anaesthesia as an outpatient procedure. Indeed, the present invention is believed to realise the cheapest and most efficient universally applicable instrument for treating pre-cancerous conditions of the cervix.

These advantages can be gained in other specific ways within the inventive concept, and many other variations are possible. Accordingly, reference should be made to the appended claims and to other conceptual statements herein rather than to the foregoing specific description when defining the inventive concept. In particular, whilst the instrument of this invention has been described for the treatment of uterine cervical conditions, it is envisaged that aspects of the invention could be used with benefit in the investigation or treatment of other lesions and other conditions, whether external or internal.

What is claimed is:

1. A cervical biopsy instrument comprising:
   a shaft defining a longitudinal axis and having a proximal end and a distal end;
   at least one arm extending laterally from the shaft;
   a cutting wire capable of cutting tissue when current is supplied to the wire in use through conductor means in the shaft, a cutting portion of the cutting wire being supported at an outer end by the arm and being inclined relative to the longitudinal axis such that the cutting portion of the wire converges with the longitudinal axis moving from the arm towards the distal end; and
   means for adjusting and setting the inclination and/or length of the cutting portion;
   wherein the arm is variable in length with respect to the longitudinal axis to vary the distance of the outer end of the cutting portion from the longitudinal axis.

2. The instrument of claim 1, wherein the cutting portion extends from the outer end supported by the arm to an inner end supported by the shaft at or near the distal end.

3. The instrument of claim 1, wherein a plurality of arms extend laterally from and are angularly spaced about the shaft, each arm supporting a respective cutting portion at an inclination relative to said longitudinal axis such that the cutting portions converge with the longitudinal axis approaching the distal end.

4. The instrument of claim 3, wherein first and second arms are opposed about the shaft so that the cutting portions of cutting wire supported by those arms are substantially coplanar.

5. The instrument of claim 1, wherein the or each arm is movable during adjustment in a direction parallel to the longitudinal axis with respect to the distal end of the shaft.

6. The instrument of claim 5, wherein the shaft has graduation means visible during adjustment to indicate the longitudinal position of the or each arm with respect to the distal end of the shaft.

7. The instrument of claim 5, wherein the or each arm is mounted on a carriage mounted in turn to the shaft for movement along the shaft.

8. The instrument of claim 7, and further including means for locking the carriage to prevent movement of the carriage with respect to the shaft.

9. The instrument of claim 5, wherein a plurality of arms extend laterally from and are angularly spaced about the shaft, each arm supporting a respective cutting portion at an inclination relative to said longitudinal axis such that the cutting portions converge with the longitudinal axis approaching the distal end of the shaft, and the position of the inner end is fixed with respect to the distal end of the shaft.

10. The instrument of claim 1, wherein the or each arm is plastically deformable and can be varied in length by varying its curvature.

11. The instrument of claim 3, wherein each arm is variable in length independently of the or each other arm.

12. The instrument of claim 1 and including retractor means for retracting excess cutting wire if the cutting portion is shortened.

13. The instrument of claim 12 and including storage means for storing retracted cutting wire.

14. The instrument of claim 12, wherein the retractor means maintains tension on the cutting portions after adjustment.

15. The instrument of claim 12, wherein the retractor means comprises spring means acting in tension.

16. The instrument of claim 15, wherein there are first and second spring means, the first spring means being disposed distally with respect to the second spring means and the spring means being offset longitudinally from each other to an extent necessary to permit their maximum extension in use.

17. The instrument of claim 16, wherein the first and second spring means are within a tubular shaft portion and have an aggregate diameter greater than the internal diameter of the tubular shaft portion.

18. The instrument of claim 15, wherein first and second spring means are at longitudinally corresponding positions beside each other.

19. The instrument of claim 18, wherein the first and second spring means are segregated from each other.

20. The instrument of claim 15 comprising first and second wires extending to first and second cutting portions and common spring means acting on both of the first and second wires to tension and retract the cutting portions.

21. The instrument of claim 20, wherein a partition between the first and second wires has an opening through which the common spring means extends.

22. The instrument of claim 15, wherein the spring means is in series with the cutting wire and the conductor means.

23. The instrument of claim 12, wherein the cutting portion is anchored at one end and is movably supported at an other end to permit movement of the cutting wire with respect to the movable support during retraction or paying out.

24. The instrument of claim 23, wherein the movable support is at an inner end of the cutting portion.

25. The instrument of claim 1 and including centering means movable along the shaft in a direction parallel to the longitudinal axis, the centering means being advanced towards the distal end of the shaft to engage, in use, within a cervical canal that is wider than the thickness of a distal portion of the shaft.

26. The instrument of claim 25, wherein the centering means defines a cervix-engaging surface that tapers towards the distal end of the shaft.

27. The instrument of claim 26, wherein the cervix-engaging surface is frusto-conical.

28. The instrument of claim 25, wherein the centering means has a parked position disposed proximally with respect to the or each arm.

29. The instrument of claim 25, wherein the centering means can be advanced into a cervix-engaging position disposed distally with respect to the or each arm.

30. The instrument of claim 25, wherein the centering means is a collar around the shaft.

31. The instrument of claim 30, wherein the collar resiliently grips the shaft.

32. The instrument of claim 30, wherein the centering means and the shaft have complementary threads by which the centering means can be moved longitudinally with respect to the shaft.

33. The instrument of claim 1, and having a tapered distal end portion.

34. The instrument of claim 33, wherein the distal end portion tapers to a point defining an end of the cutting portion.

35. A cervical biopsy instrument comprising:
   a shaft defining a longitudinal axis and having a proximal end and a distal end;
   at least one arm extending laterally from the shaft;
   a cutting wire capable of cutting tissue when current is supplied to the wire in use through conductor means in the shaft, a cutting portion of the cutting wire being supported at an outer end by the arm and being inclined relative to the longitudinal axis such that the cutting portion of the wire converges with the longitudinal axis moving from the arm towards the distal end;
   means for adjusting and setting the inclination and/or length of the cutting portion; and
   centering means movable along the shaft in a direction parallel to the longitudinal axis, the centering means being advanced towards the distal end of the shaft to engage, in use, within a cervical canal that is wider than the thickness of a distal portion of the shaft.

36. The instrument of claim 35, wherein the centering means defines a cervix-engaging surface that tapers towards the distal end of the shaft.

37. The instrument of claim 36, wherein the cervix-engaging surface is frusto-conical.

38. The instrument of claim 36, wherein the centering means has a parked position disposed proximally with respect to the or each arm.

39. The instrument of claim 35, wherein the centering means can be advanced into a cervix-engaging position disposed distally with respect to the or each arm.

40. The instrument of claim 35, wherein the centering means is a collar around the shaft.

41. The instrument of claim 40, wherein the collar resiliently grips the shaft.

42. The instrument of claim 40, wherein the centering means and the shaft have complementary threads by which the centering means can be moved longitudinally with respect to the shaft.

* * * * *